United States Patent
Inano et al.

(10) Patent No.: US 11,360,088 B2
(45) Date of Patent: Jun. 14, 2022

(54) METHOD FOR MEASURING INFLUENZA B VIRUS

(71) Applicant: DENKA COMPANY LIMITED, Tokyo (JP)

(72) Inventors: Koichi Inano, Gosen (JP); Takashi Miyazawa, Gosen (JP); Osamu Ishikawa, Gosen (JP)

(73) Assignee: DENKA COMPANY LIMITED, Tokyo (JP)

( * ) Notice: Subject to any disclaimer, the term of this patent is extended or adjusted under 35 U.S.C. 154(b) by 0 days.

(21) Appl. No.: 14/917,643

(22) PCT Filed: Sep. 10, 2014

(86) PCT No.: PCT/JP2014/073957
§ 371 (c)(1),
(2) Date: Mar. 9, 2016

(87) PCT Pub. No.: WO2015/037629
PCT Pub. Date: Mar. 19, 2015

(65) Prior Publication Data
US 2016/0223541 A1 Aug. 4, 2016

(30) Foreign Application Priority Data
Sep. 10, 2013 (JP) .............................. JP2013-187320

(51) Int. Cl.
*G01N 33/569* (2006.01)
*C07K 16/10* (2006.01)
*G01N 33/558* (2006.01)
*G01N 33/577* (2006.01)

(52) U.S. Cl.
CPC ... *G01N 33/56983* (2013.01); *C07K 16/1018* (2013.01); *G01N 33/558* (2013.01); *G01N 33/577* (2013.01); *G01N 2333/11* (2013.01); *G01N 2469/10* (2013.01)

(58) Field of Classification Search
None
See application file for complete search history.

(56) References Cited

U.S. PATENT DOCUMENTS

2006/0292636 A1 * 12/2006 Yarnall .............. C07K 16/1232
435/7.1

FOREIGN PATENT DOCUMENTS

| EP | 1908522 B1 * | 4/2008 | ........... G01N 33/558 |
|----|---|---|---|
| JP | 2007-285749 A | 11/2007 | |
| JP | 4932940 B2 | 5/2012 | |
| JP | 4936428 B2 | 5/2012 | |
| WO | WO 2005/007698 A1 | 1/2005 | |
| WO | WO 2009/064805 A1 | 5/2009 | |

OTHER PUBLICATIONS

Nakagawa et al. J Virol Methods 1999 vol. 79, pp. 113-120.*
Walls et al. J of clinical Microbiology Dec. 1986 (Year: 1986).*
Bucher et al. J of Virology Sep. 1989 (Year: 1989).*
Ichikawa et al., "Evaluation of a rapid detection kit for influenza A and B viruses using immuno chromatography and enzyme immunoassay," Espline Influenza A & B®, Japanese Journal of Medicine and Pharmaceutical Science, vol. 49, 2003. 11 pgs.
Kawai et al., "A comparison of the effectiveness of zanamivir and oseltamivir for the treatment of influenza A and B," J. Infect., vol. 56, No. 1, Jan. 2008 (Epub Oct. 17, 2007), 1 page.
Mitamura et al., "Diagnosis and Treatment of influenza—Clinical Investigation on Viral Shedding in Children with Influenza," Virus, vol. 56, No. 1, 2006, pp. 109-116.

* cited by examiner

*Primary Examiner* — Shanon A. Foley
*Assistant Examiner* — Myron G Hill
(74) *Attorney, Agent, or Firm* — Birch, Stewart, Kolasch & Birch, LLP

(57) ABSTRACT

A method for measuring influenza B virus by an immunoassay, which method enables specific detection of influenza B virus with a higher sensitivity than conventional methods, and a device or a kit therefor are disclosed. The method for measuring influenza B virus includes carrying out an immunoassay of influenza B virus by a sandwich method using two kinds of monoclonal antibodies each of which specifically reacts with the region of the 125th to 248th amino acids of matrix protein (M1) of influenza B virus, which two kinds of monoclonal antibodies are capable of binding to the region of the 125th to 248th amino acids of M1 at the same time, or antigen-binding fragments thereof.

24 Claims, 1 Drawing Sheet
Specification includes a Sequence Listing.

METHOD FOR MEASURING INFLUENZA B VIRUS

TECHNICAL FIELD

The present invention relates to a method for measuring influenza B virus by an immunoassay, and a device or a kit therefor.

BACKGROUND ART

Influenza is an infectious disease which is prevalent during winter. Although patients with influenza develop clinical symptoms such as high fever, upper respiratory inflammation, malaise, and the like, differential diagnosis of influenza from infectious diseases caused by other viruses such as adeno virus, RS virus, parainfluenza virus, human metapneumovirus, and the like based on these symptoms alone is not always easy.

Examples of methods for definitive diagnosis of influenza include virus isolation, serological diagnosis, and nucleic acid detection (PCR). Since these methods cannot be easily and regularly carried out at clinical sites such as consultation rooms, a simpler diagnostic method has been demanded. Recently, an antigen detection reagent based on immunochromatography was developed, and has been widely used for aiding the diagnosis since the reagent enables simple and rapid diagnosis.

However, it has been pointed out that the amount of virus contained in a sample collected from a patient is smaller in cases of influenza B than in cases of influenza A, so that the detection sensitivity obtained by using an antigen detection reagent is weaker in cases of influenza B than in cases of influenza A (Non-patent Document 1).

Influenza virus is a virus having segmental negative-strand RNA as the genomic gene, which is composed of eight segments, that is, HA, NA, PA, PB1, PB2, M, NP, and NS segments. Influenza virus can be divided into type A, type B, and type C depending on the antigenicities of matrix protein (M1) and nucleoprotein (NP), among the proteins constituting the virus. Since the proteins have different antigenicities among the types, cross-reaction does not occur between different types.

Although influenza B is indistinguishable from influenza A based on virus morphology or clinical symptoms, influenza B is important as a pathogen of human influenza similarly to the type A.

The M segment of influenza B virus encodes two different genes, M1 and BM2, and a constituent protein is synthesized from each gene. These proteins correspond to M1 and M2 of influenza A virus, but BM2 of the type B has a structure largely different from that of M2 of the type A. M1 is localized such that the inside of the viral envelope is lined therewith, and it is thought that M1 substantially plays a role as a shell.

As therapeutic agents for influenza, oseltamivir phosphate, zanamivir hydrate, peramivir hydrate, laninamivir octanoate hydrate, and amantadine hydrochloride are used. Since amantadine hydrochloride, which is an M2 inhibitor, does not inhibit infection and growth of influenza B virus, it is used for treatment of only influenza A virus. Although the former four therapeutic agents have the same site of action as neuraminidase (NA) inhibitors, they have been pointed out to show different effectiveness among the different types of influenza in terms of the time required for reduction of fever, the virus survival rate, and the like (Non-patent Document 2). Thus, differential diagnosis of the type of influenza is important for appropriate selection of the therapeutic agent to be used thereafter.

In conventional detection of influenza, an anti-NP antibody (Patent Documents 1 to 3), anti-M2 antibody (Patent Document 4), or the like has been used. However, an anti-M1 antibody that specifically reacts with M1 has not been used.

PRIOR ART DOCUMENTS

Patent Documents

[Patent Document 1] JP 2007-285749 A
[Patent Document 2] JP 4936428 B
[Patent Document 3] WO 2005/007698
[Patent Document 4] JP 4932940 B Non-Patent Documents

[Non-patent Document 1] Virus vol. 56(1), pp. 109-116, 2006 (Diagnosis and Treatment of Influenza)
[Non-patent Document 2] J Infect. 2008 January; 56(1): 51-7. Epub 2007 Oct. 15. (A comparison of the effectiveness of zanamivir and oseltamivir for the treatment of influenza A and B.)
[Non-patent Document 3] Orthomyxoviridae, Fields Virology. 4th edition. 2001

SUMMARY OF THE INVENTION

Problems to be Solved by the Invention

In conventional immunoassays, anti-NP monoclonal antibodies and the like have been used. However, since these showed lower reactivity with influenza B virus, an antibody having higher reactivity has been demanded.

An object of the present invention is to provide a method for measuring influenza B virus by an immunoassay, which method enables specific detection of influenza B virus with a higher sensitivity than conventional methods, and a device or a kit therefor.

Means for Solving the Problems

As a result of intensive study, the present inventors discovered that, by a sandwich method using two kinds of monoclonal antibodies whose epitopes are particular regions of M1 protein of influenza B virus, influenza B virus can be specifically detected with a higher sensitivity than conventional methods, thereby completing the present invention.

That is, the present invention provides a method for measuring influenza B virus, the method comprising carrying out an immunoassay of influenza B virus by a sandwich method using two kinds of monoclonal antibodies each of which specifically reacts with the region of the 125th to 248th amino acids of matrix protein (M1) of influenza B virus, the two kinds of monoclonal antibodies being capable of binding to the region of the 125th to 248th amino acids of M1 at the same time, or antigen-binding fragments thereof. The present invention also provides an immunoassay device or a kit for measuring influenza B virus, comprising two kinds of monoclonal antibodies each of which specifically reacts with the region of the 125th to 248th amino acids of matrix protein (M1) of influenza B virus, the two kinds of monoclonal antibodies being capable of binding to the region of the 125th to 248th amino acids of M1 at the same time, or antigen-binding fragments thereof.

Effect of the Invention

By the immunoassay of the present invention, influenza B virus can be detected distinctly from influenza A virus by targeting of a protein which is different from conventional targets. Moreover, by using the immunoassay device or the kit provided by the present invention, influenza B virus can be specifically and highly sensitively detected, so that the present invention may largely contribute to diagnosis and treatment of influenza.

MODE FOR CARRYING OUT THE INVENTION

Figure 1:
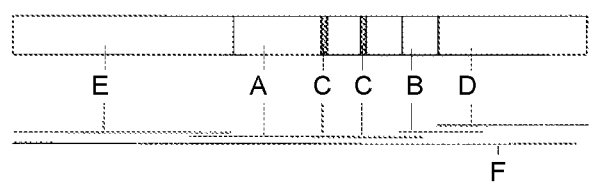
FIG. 1 is a diagram schematically illustrating a preferred embodiment of the immunochromatographic immunoassay device of the present invention.

The monoclonal antibody used in the present invention undergoes antigen-antibody reaction with influenza B virus M1 (hereinafter referred to as B-M1). B-M1 is a protein constituted by 248 amino acid residues, and its signal due to antigen-antibody reaction can be specifically detected at a molecular weight of 20 to 35 kD when the antibody is used for detection by Western blotting. The term "specific" in the present description means that, in a liquid system containing a mixture of proteins and the antibody, the antibody does not cause antigen-antibody reaction with the proteins other than B-M1 at a detectable level, or, even in cases where the antibody causes a certain binding reaction or association reaction with a protein other than B-M1, the reaction is evidently weaker than the antigen-antibody reaction between the antibody and B-M1. The monoclonal antibody used in the present invention reacts with the region of the 125th to 248th amino acids in the B-M1 amino acid sequence. Amino acid sequences of B-M1 are known, and described in, for example, GenBank: AEN79424 (SEQ ID NO:1).

An antigen-binding site alone separated from the monoclonal antibody of the present invention may be used for the reaction. That is, fragments having specific antigen-binding capacity (antigen-binding fragment), such as Fab, Fab', F(ab')$_2$, and single-chain antibodies (scFv) prepared by known methods are included within the scope of the present invention. The class of the monoclonal antibody is not limited to IgG, and may also be IgM or IgY.

Influenza B virus can be divided into two groups having different antigenicities and belonging to different genetic lineages, that is, the Yamagata lineage and the Victoria lineage. In a preferred embodiment, the monoclonal antibody of the present invention specifically reacts with B-M1 of virus strains belonging to either lineage. More preferably, the monoclonal antibody of the present invention specifically reacts with M1 of any known influenza B virus strain.

In a preferred embodiment, the monoclonal antibody used in the present invention does not undergo antigen-antibody reaction with pathogens of other infectious diseases. For example, the monoclonal antibody does not undergo antigen-antibody reaction with influenza A virus, adeno virus, Coxsackie virus, echovirus, herpes simplex virus, measles virus, mumps virus, parainfluenza virus, RS virus, *Chlamydia psittaci, Chlamydia trachomatis, Mycoplasma pneumoniae, Bordetella pertussis, Escherichia coli, Haemophilus influenzae, Legionella pneumophila, Listeria monocytogenes, Pseudomonas aeruginosa, Serratia marcescens, Staphylococcus aureus, Staphylococcus epidermidis, Streptococcus pneumoniae, Streptococcus pyogenes*, group B streptococci, group C streptococci, or group G streptococci.

The monoclonal antibody used in the present invention may be obtained by immunizing an animal with B-M1 or a partial peptide thereof (the polypeptide composed of the region of the 125th to 248th amino acids, or a partial peptide thereof) by a known immunological method, and then preparing a hybridoma using cells of the immunized animal. The length of the peptide used for the immunization is not limited. Preferably, a peptide of not less than 5 amino acids, more preferably not less than 10 amino acids, may be used to provide the immunogen.

The B-M1 to be used as the immunogen can be obtained from a cultured virus liquid, or can be obtained by incorporating DNA encoding B-M1 into a plasmid vector, and introducing the resulting vector to a host cell, followed by allowing expression of the B-M1.

Alternatively, the B-M1 or the partial peptide thereof to be used as the immunogen can be expressed as a fusion protein with a protein exemplified below, and the expressed fusion protein can be used as the immunogen after purification or without purification. The preparation of the fusion protein can be carried out using, for example, Glutathion S-transferase (GST), maltose-binding protein (MBP), thioredoxin (TRX), Nus-tag, S-tag, HSV-tag, FRAG tag, polyhistidine tag, or the like which is commonly used as a "protein expression/purification tag" by those skilled in the art. Preferably, the fusion protein with such a protein is cleaved into the portion of M1 or the partial peptide thereof, and the tag portion, using a digestive enzyme, and subjected to separation/purification before use as the immunogen.

The preparation of the monoclonal antibody from the immunized animal can be easily carried out by the well-known method of Kohler et al. (Kohler et al., Nature, vol. 256, p. 495-497 (1975)). That is, antibody-producing cells such as spleen cells or lymphocytes are recovered from the immunized animal, and the recovered cells are fused with mouse myeloma cells by a conventional method to prepare hybridomas. The resulting hybridomas are cloned by the limiting dilution method or the like. Thereafter, a monoclonal antibody that undergoes antigen-antibody reaction with a polypeptide composed of the sequence of the 125th to 248th amino acids of B-M1 (hereinafter referred to as "B-M1C") is selected from the monoclonal antibodies produced by the cloned hybridomas.

Purification of the monoclonal antibody from ascites or a culture supernatant may be carried out by a known immunoglobulin purification method. Examples of the method include fractionation by salting out using ammonium sulfate or sodium sulfate, PEG fractionation, ethanol fractionation, DEAE ion-exchange chromatography, and gel filtration. Depending on the species of the immunized animal and the class of the monoclonal antibody, affinity chromatography using a carrier to which any of protein A, protein G, and protein L is bound may be used for the purification.

In the method for measuring influenza B virus of the present invention, an immunoassay is carried out by a sandwich method using two kinds of anti-influenza B virus M1C antibodies prepared as described above (each of which may be hereinafter referred to as "anti-B-M1C antibody").

In order to perform the sandwich method, these two kinds of monoclonal antibodies need to be capable of binding to B-M1C at the same time, so that such a combination of the antibodies is selected. The sandwich method per se is well known in the field of immunoassays, and can be carried out by, for example, immunochromatography or ELISA. These sandwich methods per se are well known, and the method of the present invention can be carried out in the same manner as a well-known sandwich method except that the two kinds of anti-B-M1C antibodies described above are used. In the present invention, "measurement" includes any of quantification, semi-quantification, and detection.

In the immunoassay based on the detection principle of a sandwich method, any solid phase may be used as the solid phase on which the antibody is to be immobilized, as long as the antibody can be immobilized thereon by a known technique. The solid phase may be arbitrarily selected from known solid phases such as porous thin films (membranes) having a capillary action; particles, test tubes, and resin plates. Examples of the substance for labeling the antibody include enzymes, radioisotopes, fluorescent substances, luminescent substances, colored particles, and colloidal particles.

Among the above-mentioned immunoassay methods using various materials, lateral-flow immunoassay methods using a membrane are preferred from the viewpoint of enabling simple and rapid clinical tests.

The present invention also provides an immunoassay device which enables a lateral-flow immunoassay using an anti-B-M1 antibody. The immunoassay device provided by the present invention is composed of a support having a detection area in which an antibody (Antibody 1) for capturing the subject to be measured (antigen) is immobilized; a label area having a movable labeled antibody (Antibody 2), a sample pad to which a sample is added dropwise, an absorption zone which absorbs a developed sample liquid, and a backing sheet for laminating these members together, wherein at least one of Antibody 1 and Antibody 2 is the anti-B-M1 antibody of the present invention.

The number of detection areas, and the number of types of the labeled antibody contained in the label area, are not limited to one. By using antibodies corresponding to a plurality of subjects to be measured, two or more antigens can be detected in a single immunoassay device.

FIG. 1 is a diagram illustrating a preferred embodiment of the immunoassay device of the present invention. A represents a support; B represents a label area; C represents a detection area; D represents a sample pad; E represents an absorption zone; and F represents a backing sheet.

In FIG. 1, the upper panel shows a top view, and the lower panel shows a cross-sectional view. In the case shown in this figure, a support wherein two detection areas are formed on a backing sheet; an absorption zone; a label area; and a sample pad; are laminated together. As shown in the figure, an end of the absorption zone overlaps with an end of the support; the other end of the support overlaps with an end of the label area; and the other end of the label area overlaps with an end of the sample pad. By this, a continuous lateral-flow channel is formed.

The support is a material having a property which allows immobilization of the antibody for capturing the antigen, as well as a property which does not prevent horizontal movement of a liquid. The support is preferably a porous thin film having a capillary action, which is a material capable of transporting, by absorption, a liquid and a component dispersed in the liquid. The material constituting the support is not limited, and examples of the material include cellulose, nitrocellulose, cellulose acetate, polyvinylidene difluoride (PVDF), glass fiber, nylon, and polyketone. Among these, a thin film prepared using nitrocellulose is more preferred.

The label area is composed of a porous base material containing a labeled antibody. The material of the base material may be a glass fiber, non-woven fabric, or the like which is commonly used. The base material is preferably pad-shaped and has a thickness of about 0.3 mm to 0.6 mm from the viewpoint of allowing impregnation with a large amount of labeled antibody.

The detection area means a partial area(s) of the support on which the antibody for capturing the antigen is immobilized. From the viewpoint of practically aiding diagnosis, the detection area preferably has at least one area where the anti-B-M1 antibody for capturing the B-M1 antigen is immobilized, as well as a detection area for detection of influenza A virus.

The sample pad is a portion to which a sample, or a specimen prepared using a sample, is added dropwise. The sample pad is a water-absorptive, porous material. The material of the sample pad may be cellulose, glass fiber, non-woven fabric, or the like which is commonly used. For use of a large amount of sample in the immunoassay, the sample pad preferably has a pad shape having a thickness of about 0.3 mm to 1 mm. It should be noted that the distinction between the sample pad and the label area is merely based on their functions, and they do not necessarily need to be separate materials. That is, a partial area in the material placed as the sample pad may have a function as the label area.

The absorption zone is a member for absorbing components that are supplied but not involved in the reaction in the detection area. The material of the absorption zone may be a filter paper, sponge, or the like having high water holding capacity composed of a common natural macromolecular compound, synthetic macromolecular compound, or the like. For promotion of development of the sample, the absorption zone preferably has high water-absorbing capacity.

The backing sheet is a member on which all of the above-described materials, that is, the support, sample pad, label area, and absorption zone, are attached/immobilized such that they partially overlap with each other. The backing sheet is not necessarily required as long as these materials are arranged/immobilized at optimal intervals, but it is generally preferred to use the backing sheet from the viewpoint of convenience in production and/or use of the device.

In the immunoassay device of the embodiment illustrated in FIG. 1, the sample passes through a porous channel formed by a series of the members, that is, the sample pad, label area, support, detection area, and absorption zone, which are connected to each other. Therefore, in the present embodiment, all of these members constitute the sample movement area. Depending on the material and the shape of each constituting material, the sample may pass through an interface without impregnation into the material. Since the sample movement area defined in the present description may be located either inside the material or on an interface of the material, the immunoassay device of this embodiment is also included within the scope of the present description.

A method for using the immunoassay device of the present invention is described below based on the embodiment shown in FIG. 1.

The measurement is begun by adding a sample, or a specimen prepared using a sample, dropwise to the sample pad. The test sample to be added dropwise is preferably about 2- to 20-fold diluted in advance using a buffer containing a surfactant.

The test sample added dropwise to the sample pad is developed in the horizontal direction by the capillary action, sequentially through the label area, support, and absorption zone. As the development of the test sample proceeds, a labeled antibody is released into the liquid in the label area, and developed into the support. In cases where an antigen is present in the test sample, the antigen is specifically captured by a capture antibody in the detection area of the support, and, in addition, the antigen also forms a complex with the labeled antibody by specific reaction. By this, sandwiching of the antigen between the antibodies is achieved in the detection area, and the labeled antibody-antigen complex can be detected in the detection area.

EXAMPLES

The present invention is described below by way of Examples. However, the present invention is not limited to the following Examples.

Example 1

Preparation of Anti-influenza B Virus M1 Monoclonal Antibody

1. Preparation of Influenza B Virus M1 Antigen

Based on a cDNA library constructed from viral RNA of the B/Florida/4/2006 strain by reverse transcription, DNA encoding M1 was subcloned into a plasmid vector. An *E. coli* strain in which the plasmid vector was introduced was subjected to aeration/agitation culture to allow expression of the M1. The M1 was recovered by disruption of the bacterial cells and subsequent centrifugation. The recovered M1 was purified by chromatography. In the present description, the purified product is referred to as "purified M1 antigen".

2. Preparation of Anti-influenza B Virus M1 Monoclonal Antibody

BALB/c mice were immunized with the purified M1 antigen, and kept for a certain period. From each mouse, the spleen was removed, and fusion with mouse myeloma cells (P3×63) was carried out by the method of Kohler et al. (Kohler et al., Nature, vol. 256, p. 495-497 (1975)). The resulting fused cells (hybridomas) were kept in an incubator at 37° C. The cells were then purified (into monoclonal cells) while the antibody activity in the supernatant was checked by ELISA using a plate on which the purified M1 antigen is immobilized. The obtained cell line was intraperitoneally administered to pristane-treated BALB/c mice. About two weeks later, antibody-containing ascites was collected. From the ascites obtained, IgG was purified by affinity chromatography using a protein A column, to obtain a purified anti-influenza B virus M1 antibody.

Reference Example 1

1. Preparation of Anti-influenza B Virus NP Monoclonal Antibody

BALB/c mice were immunized with an influenza B virus antigen, and kept for a certain period. From each mouse, the spleen was removed, and fusion with mouse myeloma cells (P3×63) was carried out by the method of Kohler et al. (Kohler et al., Nature, vol. 256, p. 495-497 (1975)). The resulting fused cells (hybridomas) were kept in an incubator at 37° C. The cells were then purified (into monoclonal cells) while the antibody activity in the supernatant was checked by ELISA using a plate on which an influenza B virus NP antigen is immobilized. The obtained cell line was intraperitoneally administered to pristane-treated BALB/c mice. About two weeks later, antibody-containing ascites was collected.

From the ascites obtained, IgG was purified by affinity chromatography using a protein A column, to obtain a purified anti-influenza B virus NP antibody. In the present description, the purified antibody is referred to as "anti-B-NP antibody".

Example 2

Influenza Virus Antigen Detection Reagent Using Colored Polystyrene Particles

1. Immobilization of Anti-Influenza B Virus M1 Antibody on Nitrocellulose Membrane The anti-B-M1 antibody purified in Example 1 was diluted to 1.0 mg/mL with purified water. The resulting dilution was linearly applied to a predetermined position of a nitrocellulose membrane lined with a PET film. The membrane was then dried at 45° C. for 30 minutes to obtain a membrane on which the anti-influenza B virus M1 antibody is immobilized. In the present description, the membrane obtained is referred to as "anti-M1 antibody-immobilized membrane".

2. Immobilization of Anti-Influenza B Virus NP Antibody on Nitrocellulose Membrane Using the anti-NP antibody prepared in Reference Example 1, a membrane on which the anti-influenza B virus NP antibody is immobilized was obtained by the same method as in Example 2-1. In the present description, the membrane obtained is referred to as "anti-NP antibody-immobilized membrane".

3. Immobilization of Anti-Influenza B Virus M1 Antibody on Colored Polystyrene Particles The anti-B-M1 antibody prepared in Example 1 was diluted to 1.0 mg/mL with purified water. To the resulting dilution, colored polystyrene particles were added at 0.1%, and the resulting mixture was stirred. Carbodiimide was then added to the mixture at 1%, and the resulting mixture was stirred. After removing the supernatant by centrifugation, the precipitate was resuspended in 50 mM Tris (pH 9.0) supplemented with 3% BSA, to obtain colored polystyrene particles to which the anti-influenza B virus M1 antibody is bound. In the present description, the particles obtained are referred to as "anti-M1 antibody-immobilized particles".

4. Immobilization of Anti-Influenza B Virus NP Antibody to Colored Polystyrene Particles Using the anti-B-NP antibody prepared in Reference Example 1, colored polystyrene particles to which the anti-influenza B virus NP antibody is bound were obtained by the same method as in Example 2-3. In the present description, the particles obtained are referred to as "anti-NP antibody-immobilized particles".

5. Application/Drying of Colored Polystyrene Particles to which Anti-Influenza B Virus Antibody is Bound A predetermined amount, 1.0 μg, of the antibody-immobilized particles prepared in 3 or 4 were applied to a glass-fiber non-woven fabric, and the non-woven fabric was then dried at 45° C. for 30 minutes. In the present description, the non-woven fabric obtained is referred to as "dry pad".

6. Preparation of Influenza B Virus Test Pieces

The antibody-immobilized membrane prepared in 1 or 2, and the dry pad prepared in 5, were laminated with other members (backing sheet, absorption zone, and sample pad), and the resulting laminate was cut into a piece with a width of 5 mm, to provide an influenza B virus test piece. In the present description, the influenza B virus test piece is referred to as "test piece". In the preparation of the test piece, the combination of the antibody-immobilized membrane and the dry pad to be laminated was selected such that at least one of these contains the anti-B-M1 antibody.

7. Detection of Influenza B Virus Antigen

To the sample pad of the test piece prepared in 6, 60 μL of a sample suspension containing an influenza B virus antigen (10 mM ADA (pH 6.0), 1% polyoxyethylene alkyl ether) was added dropwise, and the resulting mixture was left to stand for 8 minutes. In cases where antibody-immobilized particles which had reacted with the antigen were captured at the position where the antibody was applied on the antibody-immobilized membrane, and coloring due to the capture could be visually observed, the test piece was evaluated as "+". In cases where no coloring could be visually observed, the test piece was evaluated as "−". In this test, the test pieces containing any of the combinations, that is, the test pieces containing a combination in which one or both of the antibody-immobilized membrane and the dry pad contain(s) the anti-B-M1 antibody, were evaluated as "+".

Example 3

Detection of Antigen by Western Blotting Using Anti-Influenza B Virus Monoclonal Antibody 1. Preparation of Influenza B Virus Recombinant M1

Based on the cDNA library constructed in Example 1-1, each of DNA encoding the 1st to 124th amino acids and DNA encoding the 125th to 248th amino acids in an M1 amino acid sequence was subcloned into a plasmid vector. An *E. coli* strain in which the plasmid vector was introduced was subjected to aeration/agitation culture to allow expression of the recombinant M1. Each recombinant M1 was recovered by disruption of the bacterial cells and subsequent centrifugation. The recovered recombinant M1 was purified by chromatography. In the present description, the recombinant M1 composed of the former amino acid sequence is referred to as "M1-N", and the recombinant M1 composed of the latter amino acid sequence is referred to as "M1-C".

2. Confirmation of Reactivity by Western Blotting

Figure 2:
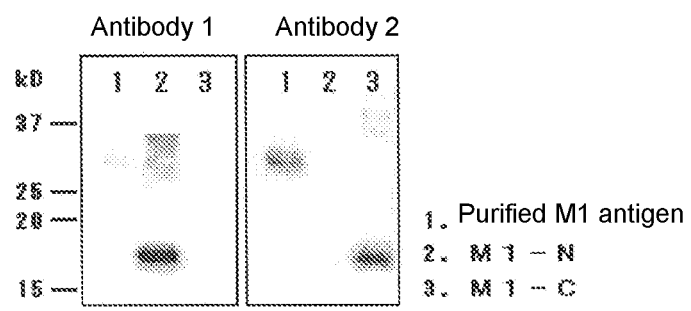
FIG. 2 is a diagram showing results of Western blotting which was carried out using monoclonal antibodies in the Examples below.

Reactivity of the antibody obtained in Example 1 was confirmed using the purified M1 antigen, M1-N, and M1-C. SDS-PAGE was carried out by a conventional method using 10% acrylamide gel. Thereafter, protein was transferred to a PVDF membrane. After blocking of the membrane using skim milk, the membrane was sufficiently washed with PBS-Tween. The membrane was then allowed to react with the anti-B-M1 antibody whose concentration was adjusted to 1 μg/mL using PBS-Tween, at room temperature for 1 hour. After sufficiently washing the membrane with PBS-Tween, the membrane was allowed to react with a 3000-fold diluted HRP-labeled anti-mouse antibody at room temperature for 1 hour. After sufficiently washing the membrane with PBS-Tween, signals were detected using a chemiluminescence detection reagent. The antibody tested could be confirmed to be reactive with the purified M1 antigen. An antibody reactive with M1-N and an antibody reactive with M1-C could be identified. The results are shown in FIG. 2. In the present description, the former antibody is referred to as "anti-M1-N antibody", and the latter antibody is referred to as "anti-M1-C antibody".

Example 4

Confirmation of Performances of Antigen Detection Reagents Containing Combinations of Anti-M1-N Antibody and Anti-M1-C Antibody 1. Preparation of Test Pieces Containing Combinations of Anti-M1-N Antibody and Anti-M1-C Antibody By the same method as in Example 2-6, the following test pieces were prepared: a test piece having an antibody-immobilized membrane and a dry pad both of which contain the anti-M1-N antibody (NN test piece); a test piece having an antibody-immobilized membrane and a dry pad both of which contain the anti-M1-C antibody (CC test piece); a test piece having an antibody-immobilized membrane containing the anti-M1-N antibody, and a dry pad containing the anti-M1-C antibody (NC test piece); and a test piece having an antibody-immobilized membrane containing the anti-M1-C antibody, and a dry pad containing the anti-M1-N antibody (CN test piece).

2. Preparation of Test Piece Containing Combination of Anti-NP Antibody

As a control, a test piece was prepared using the anti-NP-immobilized membrane and the anti-NP-immobilized particles by the same method as in Example 2-6 (conventional test piece).

3. Comparison of Influenza B Virus Antigen Detection Sensitivity Among Test Pieces To the sample pad of the test piece prepared in 1 or 2, 60 μL of a sample suspension containing an influenza B virus antigen (10 mM ADA (pH 6.0), 1% polyoxyethylene alkyl ether) was added dropwise, and the resulting mixture was left to stand for 8 minutes. In cases where antibody-immobilized particles which had reacted with the antigen were captured at the position where the antibody was applied on the antibody-immobilized membrane, and coloring due to the capture could be visually observed, the test piece was evaluated as "+". In cases where no coloring could be visually observed, the test piece was evaluated as "−". The CC test piece showed four times higher detection sensitivity than the conventional test piece. The results are shown in Table 1.

TABLE 1

Performances of antigen detection reagents containing combinations of an anti-M1-N antibody and an anti-M1-C antibody

| Test piece | Dilution rate of the antigen | | | |
| --- | --- | --- | --- | --- |
| | ×1 | ×2 | ×8 | ×32 |
| Conventional method | + | + | + | − |
| CC | + | + | + | + |
| NC | + | + | − | − |
| CN | + | − | − | − |
| NN | − | − | − | − |

DESCRIPTION OF SYMBOLS

A. Support
B. Label area
C. Detection area
D. Sample pad
E. Absorption zone
F. Backing sheet

The invention claimed is:

1. A method for detecting influenza B virus in an immunoassay, said method comprising:
    binding a labelled monoclonal antibody or antigen binding fragment thereof to matrix protein (M1) of influenza B virus, said M1 located in the matrix of the influenza virus, wherein the labelled monoclonal antibody or antigen binding fragment thereof reacts specifically with the region of the $125^{th}$ to $248^{th}$ amino acids of M1 having SEQ ID NO: 1,
    binding influenza B virus complexed to the labelled monoclonal antibody to a support via an immobilized monoclonal antibody or antigen binding fragment thereof specific to matrix protein (M1) of influenza B virus, said M1 located in the matrix of the influenza B virus, wherein the immobilized monoclonal antibody or antigen binding fragment thereof reacts specifically with the region of the $125^{th}$ to $248^{th}$ amino acids of M1 having SEQ ID NO: 1,
    detecting the presence of the influenza B virus by detecting the presence of the label over the support having the immobilized monoclonal antibody coupled to M1 protein coupled to the labelled monoclonal antibody.

2. The method according to claim 1, wherein said immunoassay is immunochromatography.

3. The method according to claim 1, wherein said immunoassay is an ELISA method.

4. An immunoassay device or a kit for measuring influenza B virus, comprising two monoclonal antibodies each of which specifically reacts with the region of the 125th to 248th amino acids of matrix protein (M1) of influenza B virus, or antigen-binding fragments thereof, wherein the matrix protein (M1) has SEQ ID NO: 1.

5. An immunochromatographic immunoassay device comprising: a detection area in which a first antibody suitable to specifically react with the region of the 125th to 248th amino acids of matrix protein (M1) of influenza B virus, or an antigen-binding fragment thereof, is immobilized on a support; a label area in which a second antibody suitable to specifically react with the region of the 125th to 248th amino acids of matrix protein (M1) of influenza B virus, or an antigen-binding fragment thereof, is supplied together with a sample; and a sample movement area, wherein the matrix protein (M1) has SEQ ID NO: 1.

6. The immunoassay device or the kit for measuring influenza B virus according to claim 4, comprising: a support on which a first antibody as one of said monoclonal antibodies, or an antigen-binding fragment thereof, is immobilized; and a second antibody as the other monoclonal antibody, or an antigen-binding fragment thereof.

7. The method according to claim 1, wherein the immobilized and labelled antibody or antigen binding fragment thereof are the same monoclonal clone.

8. The method of claim 1, wherein the label on the labelled antibody is a fluorescent label or an enzyme label.

9. The method of claim 8, wherein the support has a capillary action.

10. The method of claim 9, wherein the support comprises cellulose, nitrocellulose, cellulose acetate, polyvinylidene difluoride (PVDF), glass fiber, nylon, or polyketone.

11. The method of claim 8, wherein the support comprises nitrocellulose.

12. The method of claim 1, wherein the support is within a device further comprising a sample pad, a label area containing the labelled antibody, and an absorption zone, said method further comprises adding a sample to the sample pad, wherein capillary action develops the device by drawing the sample sequentially from the sample pad to the label area to the support and to the absorption zone.

13. The method of claim 12, wherein the sample is added to the sample pad dropwise after being diluted 2 to 20 fold in advance using a buffer containing a surfactant.

14. The method of claim 12, wherein the label area comprises glass fiber or non-woven fabric and has a thickness of 0.3 mm to 0.6 mm.

15. The method of claim 14, wherein the absorption zone comprises filter paper or a sponge.

16. The method of claim 15, wherein the label on the labelled antibody is a fluorescent label or an enzyme label.

17. The method of claim 16, wherein the support comprises cellulose, nitrocellulose, cellulose acetate, polyvinylidene difluoride (PVDF), glass fiber, nylon, or polyketone.

18. The method of claim 1, wherein said labeled antibody or antigen binding fragment thereof and said immobilized antibody or antigen binding fragment thereof are both monoclonal antibodies or an antigen binding fragment thereof produced by immunizing an animal with said peptide and preparing hybridoma cells using antibody producing cells from said immunized animal.

19. The method of claim 1, wherein said labeled antibody or antigen binding fragment thereof and said immobilized antibody or antigen binding fragment thereof are both monoclonal antibodies or an antigen binding fragment thereof produced by immunizing an animal with said peptide, recovering antibody producing cells comprising at least spleen or lymphocyte cells from said animal and fusing said antibody producing cells with mouse myeloma cells to prepare hybridoma cells that react with said peptide.

20. The method of claim 19, which further comprises cloning said hybridoma cells that react with said peptide.

21. The method of claim 19, wherein said antibody producing cells comprise spleen cells.

22. The method of claim 18, wherein said animal is a mouse.

23. The method of claim 22, wherein said mouse is a BALB/c mouse.

24. The method of claim 12, wherein said device comprises a detection area in which said immobilized antibody is immobilized and a backing sheet below said support, said label area, said detection area, said sample pad and said adsorption zone.

* * * * *

SEQUENCE LISTING

<160> NUMBER OF SEQ ID NOS: 1

<210> SEQ ID NO 1
<211> LENGTH: 248
<212> TYPE: PRT
<213> ORGANISM: Influenza B virus

<400> SEQUENCE: 1

```
Met Ser Leu Phe Gly Asp Thr Ile Ala Tyr Leu Leu Ser Leu Thr Glu
1               5                   10                  15

Asp Gly Glu Gly Lys Ala Lys Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
                100                 105                 110

Phe Glu Ile Ala Glu Gly His Glu Ser Ser Ala Leu Leu Tyr Cys Leu
            115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245
```